United States Patent [19]

Mirviss

[11] Patent Number: 4,532,085
[45] Date of Patent: Jul. 30, 1985

[54] PHOSPHATE ESTER RECOVERY

[75] Inventor: Stanley B. Mirviss, Stamford, Conn.

[73] Assignee: Stauffer Chemical Company, Westport, Conn.

[21] Appl. No.: 511,072

[22] Filed: Jul. 5, 1983

[51] Int. Cl.³ .............................................. C07F 9/09
[52] U.S. Cl. .................................................... 260/990
[58] Field of Search ................................. 260/990, 966

[56] References Cited

U.S. PATENT DOCUMENTS

| 1,844,408 | 2/1932 | Nicolai | 260/990 |
| 1,994,591 | 3/1935 | Reid | 260/990 |
| 2,315,495 | 4/1943 | Beeg et al. | 260/990 |
| 2,335,511 | 11/1943 | Havemann et al. | 260/990 |

Primary Examiner—Anton H. Sutto
Attorney, Agent, or Firm—Vivienne T. White

[57] ABSTRACT

A method of recovering phosphate esters from the by-product residues derived from phosphate ester production is disclosed. The method comprises extracting the phosphate esters from the residue utilizing a hydrocarbon solvent.

12 Claims, No Drawings

PHOSPHATE ESTER RECOVERY

BACKGROUND OF THE INVENTION

1. Field of the Invention

The invention relates to the recovery of phosphate ester values from distillation residues containing amounts of phosphate esters and in particular the phosphate esters from the residue derived from the production of aryl phosphate esters.

2. Related Art

The residue by-product from the distillation of aryl phosphate esters is a viscous, black, odoriferous material having very poor flow properties. A typical residue is comprised of about 84 wt. % phosphate esters, 16 wt. % of other organics (primarily comprised of alkyl diphenyl ethers and alkylated benzenes and free phenolics), condensed phosphates and inorganics. Some of the residue is currently sold commercially under the trademark PHOSFLEX Z. The remainder of the residue is disposed of by drumming or by pumping into storage ponds.

Increasingly, however, due to the escalation of phosphate ester production, the prices of feedstock materials and increasingly stringent waste disposal regulations, new methods of recovering the phosphate esters from the residue have been sought. Such recovery would reduce the manufacturing cost for triaryl phosphates as well as decrease the volume of waste produced.

U.S. Pat. No. 1,994,591 discloses the extraction of triphenyl phosphate or other plasticizers, as listed at Col. 5, lines 9-17, from a solid nitrocellulose or cellulose acetate plastic. The process comprises initially leaching the plastic material containing the plasticizer with a solvent which dissolves both the plasticizer and the nitrocellulose subcoating and thereafter adding water to precipitate some of the nitrocellulose. Thereafter more water is added to precipitate the plasticizer and the remaining nitrocellulose. The filter cake recovered is leached with a low boiling paraffin hydrocarbon to recover the plasticizer from the solid polyhydroxylic nitrocellulose in low purity. A subsequent recrystallization is needed to attain adequate purity of the solid plasticizer.

U.S. Pat. No. 2,217,706 discloses a process similar to that disclosed in U.S. Pat. No. 1,994,591. U.S. Pat. Nos. 2,315,495 and 2,373,807 disclose processes for purifying phosphoric acid esters, such as triaryl or trialkylphosphates, from the dephenolization of waste aqueous liquors by mixing the esters to be purified with finely ground inert substances and dissolving the esters out therefrom by utilizing an aliphatic hydrocarbon.

The cited prior art were directed to the recovery of phosphate esters (generally triphenylphosphate or triaryl or trialkyl phosphates) from either waste plastic residue or from the dephenolization of waste aqueous liquors from coal or oil hydrogenation plants. In the cited art the wastes from which the phosphate esters are removed have a chemical composition which differ substantially from the waste matter being treated in the instant disclosure. For instance, the cited art are directed to recovering phosphate esters from oxygen free contaminants while the waste of the instant process comprise contaminants rich in oxygen-containing compounds.

The object of the invention therefore is to devise a means of recovering phosphate esters from waste residues containing such residues.

SUMMARY OF THE INVENTION

A method of recovering phosphate esters from triaryl phosphate distillation residue has been discovered. The method comprises extracting the phosphate esters with a hydrocarbon solvent particularly those of a saturated paraffinic type. The recovered esters have an improved color, viscosity, flowability, acidity and negligible free phenolics content.

DETAILED DESCRIPTION

The invention pertains to a method of recovering phosphate esters containing minor amounts of free phenolics from by-product waste residues from plant distillation during phosphate ester production. The free phenolics of the residue can comprise phenol, o-cresol; m/p cresol, 2,6 xylenol, 2,4 xylenol, 2,5 xylenol, 3,5 xylenol, o-ethylphenol, m/p ethylphenol, 3,4 xylenol, o/m/p isopropylphenol, o/m/p-tert-hexylphenol and 2,4-di-tert-butylphenol. The other organics comprise a mixture of alkyldiphenyl ethers and alkylated benzenes. The inorganics can comprise salts such as organophosphate of iron, magnesium, titanium and aluminum as well as completely inorganic phosphates. The condensed phosphates are mainly pyrophosphates and the like.

In the process of the invention the residue is contacted with various hydrocarbon solvents, particularly those of the saturated paraffinic type to extract the phosphate ester therefrom, and distilled to remove the solvent.

The process of the invention is applicable to the recovery of phosphate esters from the distillation residues from phosphate esters made with synthetic or natural phenolics. Examples of the former are cresols, xylenols, ethyl phenol, isopropylphenol, tert-butylphenol, tert-amylphenol and the like. Examples of the latter are phenol, cresols and xylenols.

The invention is particularly directed to recovering phosphate esters from the residue derived from the production of tert-butylphenyl phosphates such as the tert-butylphenyl diphenyl phosphate and di-tert-butylphenyl mono phenyl phosphate mixture having a Saybolt Universal Seconds (SUS) viscosity of 550 (FYRQUEL 550) or the 200-220 SUS viscosity mono-tert-butyl phenyl diphenyl phosphate (FYRQUEL 220).

In the practice of the invention the distillation residue from phosphate ester production is contacted with a saturated hydrocarbon solvent after which the solvent is recovered and distilled to recover the extracted phosphate esters.

Various hydrocarbon solvents are suitable for use in practicing the invention and particularly suitable are the saturated paraffinic type hydrocarbons or mixtures thereof, such as Varnish Makers and Painters (hereinafter VMaP naphtha) naphtha, heptane, pentane, hexane and petroleum ether.

The extractions can be accomplished at temperatures ranging from ambient to reflux. Significant differences can be realized within the above temperature range. Generally one extraction of the residue using a solvent to residue ratio of at least about 1:1 is sufficient for recovering the phosphate ester from the residue. A plurality of extractions may, however, be utilized in the practice of the invention. Ratios of solvent to residue of from about 1:1 to about 10:1 are generally desirable for economic reasons. It should be understood, however, that any amount of solvent can be utilized which is capable of recovering the ester residue.

The extraction can be accomplished by a variety of contacting methods as, for instance, by stirring to reflux for a period of time depending on the quantity and chemical composition of the residue being treated. A contact time of from about 0.3–5 hours and particularly of 0.5 to 3 hours is recommended. After the mixture is allowed to settle several hours, two solution phases result. The upper organic solvent phase can be recovered by any means recognized in the art.

The phosphate ester is readily removed from the hydrocarbon extract of the distillation residue by further distillation of the lower boiling point hydrocarbon extraction agent. The recovered hydrocarbon can then be recycled back for extraction of a fresh batch of distillation residue.

The solvent-free extract (recovered after separation from the solvent) is preferably vacuum distilled to reduce acid number and improve color prior to use.

The extracted esters were found to have improved color, with respect to the original distillation residue, viscosity, low temperature, flowability and acidity. Residue remaining after extraction of the phosphate esters, in general, exhibits good hot flow characteristics unlike the residue remaining after vacuum distillation of the distillation residue to remove phosphate esters. However, when the extraction is accomplished with VM&P naphtha an asphalt-like residue is produced upon heating.

The invention can best be illustrated from the following examples.

EXAMPLE 1

Two hundred grams of viscous residue from a variety of sources as indicated in Tables I and IA, were added to a 1 liter reactor containing a stirrer, condenser, and heating mantle together with 700 ml. of a solvent as shown in the Tables. The charge was stirred and refluxed (Table I) for two hours and then allowed to settle overnight. The upper solvent layer was decanted and stripped of solvent using a ROTOVAC ® evaporator. The brown viscous oil remaining was vacuum distilled and the ester in the amount shown was reclaimed.

TABLE I

| Example | Solvent | Hours Reflux | Hours Mixed | % Total Extract | Acid No. Extract | Gardner Color Extract |
|---|---|---|---|---|---|---|
| DISTILLATION RESIDUE SOURCE: Tertbutylphenyl phenyl phosphates PHOSFLEX-Z brand ||||||
| 1 | Hexane | 2.0 | — | 68.45 | 21.37 | — |
| 2 | Hexane | — | 2.0 | 69.70 | 20.48 | — |
| 3 | VM & P | 2.0 | — | 80.85 | 33.3 | — |
| 4 | VM & P | — | 2.0 | 65.5 | 22.7 | — |
| 5 | Heptane | — | 2.0 | 66.75 | 19.4 | — |
| 6 | Petroleum Ether | — | 2.0 | 68.35 | 23.8 | — |
| 7 | Pentane | — | 2.0 | 70.85 | 23.0 | — |
| DISTILLATION RESIDUE SOURCE: Synthetic EHC:PHOSFLEX-Z brand ||||||
| 1 | Hexane | — | 2.0 | 37.65 | 17.1 | 17 |
| 2 | VM & P | — | 2.0 | 47.85 | 17.7 | — |
| 3 | VM & P | 2.0 | — | 55.2 | 18.2 | 17 |
| 4 | Heptane | — | 2.0 | 39.75 | 13.7 | 15 |
| 5 | Pentane | — | 2.0 | 34.5 | 11.78 | — |
| 6 | Petroleum Ether | — | 2.0 | 34.1 | 13.7 | 14 |
| DISTILLATION RESIDUE SOURCE: Natural EHC:PHOSFLEX-Z brand ||||||
| 1 | VM & P | 2.0 | — | 26.35 | 7.8 | 17 |
| 2 | Hexane | 2.0 | — | 20.5 | 7.85 | 15 |
| 3 | VM & P | — | 2.0 | 37.0 | 66.2 | >18 |
| 4 | Pentane | 2.0 | — | 14.65 | 8.42 | 4 |
| 5 | Petroleum Ether | 2.0 | — | 16.55 | 10.54 | 17 |

TABLE IA

| Example | Vacuum mm. | Acid No. Distillate | % Ester Recovered | Gardner Color | Viscosity | % Residue |
|---|---|---|---|---|---|---|
| DISTILLED EXTRACT: Tertbutylphenyl phenyl phosphates PHOSFLEX-Z brand |||||||
| 1 | 0.30 | 1.12 | 44.38 | 10 | 1657 | 30.5 |
| 2 | 0.30 | 0.73 | 44.65 | 8 | 1626 | 34.4 |
| 3 | 0.30 | 0.84 | 43.93 | 12 | 1400 | 38.9 |
| 4 | 0.30 | 1.12 | 44.62 | 12 | 1534 | 33.1 |
| 5 | 0.30 | 0.84 | 43.90 | 11 | 1569 | 33.2 |
| 6 | 0.30 | 0.56 | 42.45 | 7 | 1419 | 37.5 |
| 7 | 0.30 | 0.67 | 43.23 | 8 | 1416 | 34.3 |
| DISTILLED EXTRACT: Synthetic EHC:PHOSFLEX-Z brand |||||||
| 1 | 0.30 | 2.2 | 29.81 | 5 | 192 | 20.0 |
| 2 | 1.0 | 1.4 | 33.5 | 5 | 179.9 | 26.4 |
| 3 | 0.20 | 3.9 | 40.3 | 9 | 192 | 26.2 |
| 4 | 0.30 | 2.8 | 29.6 | 6 | 194 | 26.4 |
| 5 | 0.50 | 1.96 | 35.81 | 5 | 187.2 | 17.5 |
| 6 | 0.50 | 2.8 | 28.01 | 6 | 195 | 19.1 |
| DISTILLED EXTRACT: Natural EHC:PHOSFLEX-Z brand |||||||
| 1 | 0.30 | 4.93 | 20.31 | 12 | 297 | 22.4 |
| 2 | 0.30 | 6.73 | 16.86 | 12 | 290 | 15.6 |
| 3 | 0.30 | 24.4 | 25.54 | 12 | 297 | 29.0 |
| 4 | 0.20 | 6.17 | 12.52 | 9 | 214 | 15.1 |
| 5 | 0.30 | 4.77 | 12.45 | 10 | 237 | 25.7 |

EXAMPLE II

A 200 gram sample of PHOSFLEX-Z from a waste pond consisting of mixed distillation residues from both synthetic and natural alkylphenol derived phosphate ester production was treated as in Example I using 500 ml. of a variety of hydrocarbon solvents as shown in Table II at the ambient temperature for 1 hour with vigorous stirring. Layers were allowed to separate overnight. The bottom PHOSFLEX-Z layer was again extracted with 500 ml. of the solvent previously used. The combined two upper solvent layers were distilled to remove the solvent. The results obtained are as follows:

TABLE II

| Solvent | Weight of Recovered Product/100 g. PHOSFLEX-Z | Acid Number of Product |
|---|---|---|
| Pentane | 30 g. | 18.5 |
| Hexane | 53 g. | 20.7 |
| Heptane | 37 g. | 16.8 |
| V.M. and P. Naphtha | 62 g. | 20.7 |

What is claimed:

1. A method of recovering phosphate esters from distillation residues of phosphate ester production containing polyaryl ethers and condensed phosphate impurities comprising treating the residues with a hydrocarbon solvent to extract the esters and thereafter recovering the extracted esters from the solvent.

2. The method of claim 1 wherein the residue is derived from the production of triaryl phosphate.

3. The method of claim 1 wherein the residue is derived from the production of tertbutylphenyl diphenyl phosphate.

4. The method of claim 1 wherein the residue is derived from the production of isopropylphenyl phenyl phosphates.

5. The method of claim 1 wherein the residue is derived from the production of mixed cresyl/xylenyl phenyl phosphates.

6. The method of claim 1 wherein the hydrocarbon solvent utilized is naphtha.

7. The method of claim 1 wherein the hydrocarbon solvent is heptane.

8. The method of claim 1 wherein the solvent utilized is hexane.

9. The method of claim 1 wherein the solvent utilized is petroleum ether.

10. The method of claim 1 wherein the solvent utilized is pentane.

11. The method of claim 1 wherein the ester extract is recovered from the residue by distillation.

12. The method of claim 1 wherein the solvent to residue ratio is from about 1:1 to about 10:1.

* * * * *